United States Patent [19]

Cope et al.

[11] Patent Number: 5,658,531
[45] Date of Patent: Aug. 19, 1997

[54] ASSAY DEVICE

[75] Inventors: Graham Francis Cope; Roger Bunce; John Gibbons, all of Birmingham, United Kingdom

[73] Assignee: The University of Birmingham, Birmingham, England

[21] Appl. No.: 232,173

[22] PCT Filed: Oct. 29, 1992

[86] PCT No.: PCT/GB92/01981

§ 371 Date: Dec. 21, 1994

§ 102(e) Date: Dec. 21, 1994

[87] PCT Pub. No.: WO93/09431

PCT Pub. Date: May 13, 1993

[30] Foreign Application Priority Data

Nov. 1, 1991 [GB] United Kingdom ............ 9123200
Jul. 8, 1992 [GB] United Kingdom ............ 9214457

[51] Int. Cl.$^6$ ................................ G01N 31/22
[52] U.S. Cl. ............... 422/58; 422/61; 422/102; 436/92; 436/808
[58] Field of Search ............ 422/58, 61, 102, 422/103; 436/80 E, 92

[56] References Cited

U.S. PATENT DOCUMENTS

| | | | |
|---|---|---|---|
| 2,940,448 | 6/1960 | Furlong | 422/61 |
| 3,715,189 | 2/1973 | Nighohossian et al. | 422/61 |
| 4,663,127 | 5/1987 | Jackson et al. | 422/58 |
| 4,812,293 | 3/1989 | McLauren et al. | 422/69 |
| 5,013,667 | 5/1991 | Lynn et al. | 422/61 |
| 5,179,024 | 1/1993 | Dahms | 422/61 |

FOREIGN PATENT DOCUMENTS

| | | |
|---|---|---|
| 0246760 | 11/1987 | European Pat. Off. . |
| 9014163 | 11/1990 | WIPO . |
| 93/00994 | 1/1993 | WIPO . |

OTHER PUBLICATIONS

Peach et al., "A Simple Inexpensive Urine Test of Smoking" Thorax 1985; 40:351–357.

*Primary Examiner*—Jill Warden
*Attorney, Agent, or Firm*—Jacobson, Price, Holman & Stern, PLLC

[57] ABSTRACT

A disposable assay device for assaying a sample has a body (10) including a reaction chamber (12) which contains or is adapted to receive an assay reagent sensitive to a component (e.g. nicotine metabolite) being assayed for in the sample. A sample collector/dispenser (20) has a sample collecting chamber (22) closed by an elastic membrane (24) and a downwardly projecting sampling and piercing tube (28), to enable a predetermined quantity of sample to be dispensed into the reaction chamber (12). The body (10) and the collector/dispenser (20) are non-detachably engageable together by engagement of rib (34) on collector/dispenser (20) with lip (18) on the body (10). A seal (32) seals the assembly to prevent leakage of the contents after use.

14 Claims, 4 Drawing Sheets

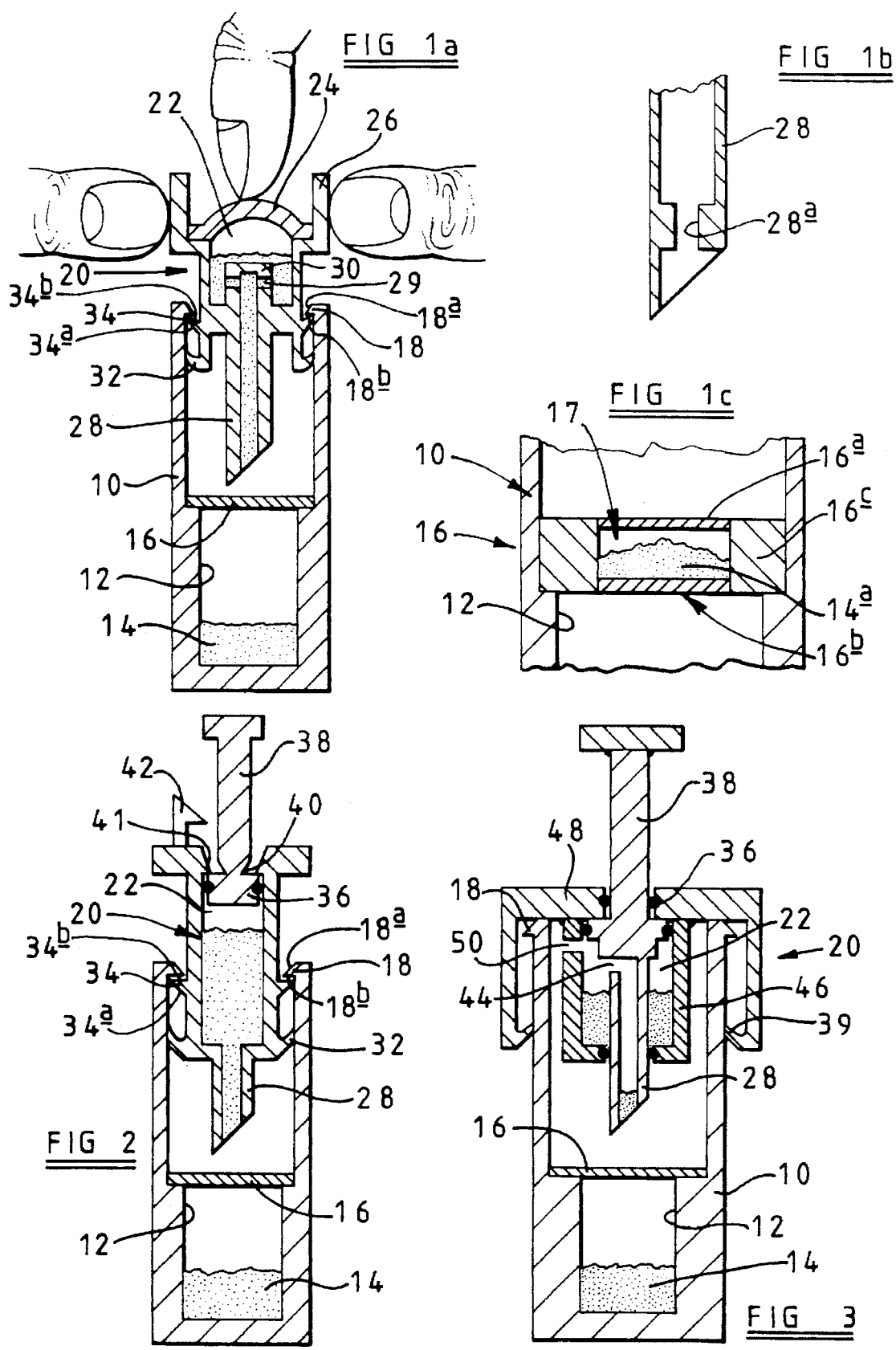

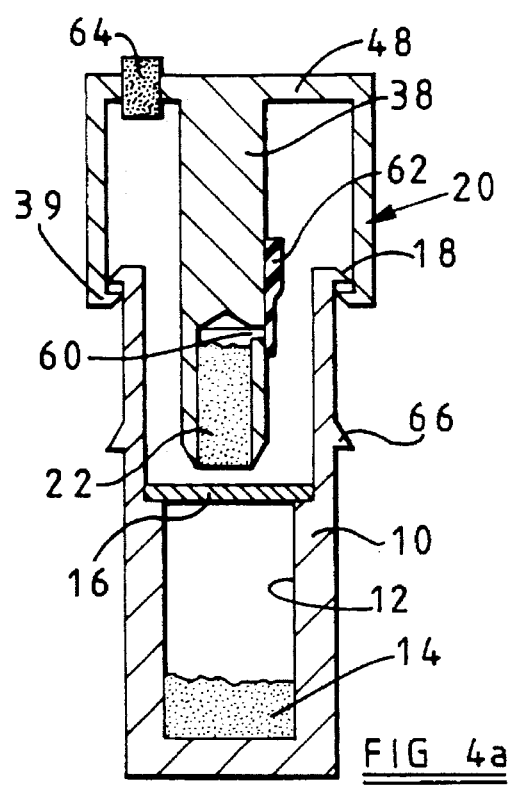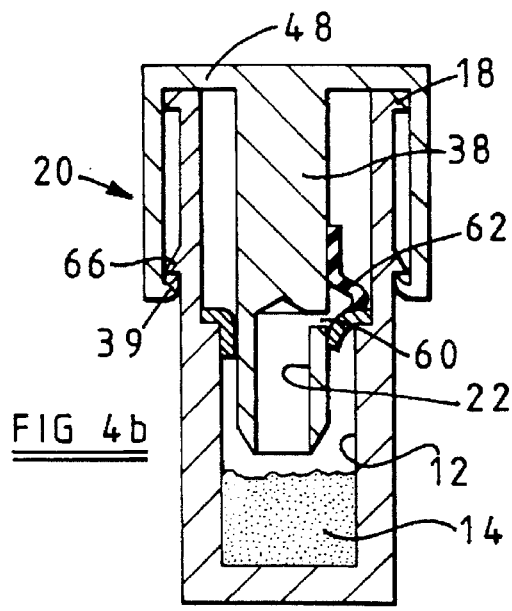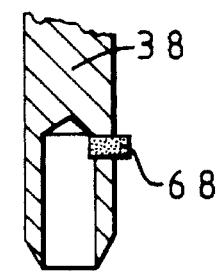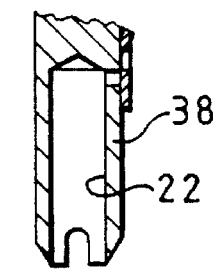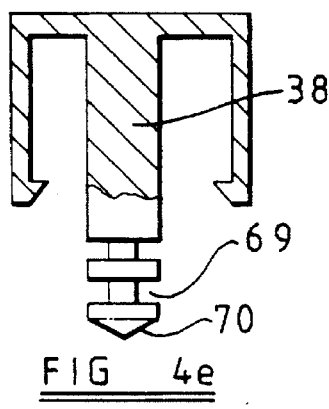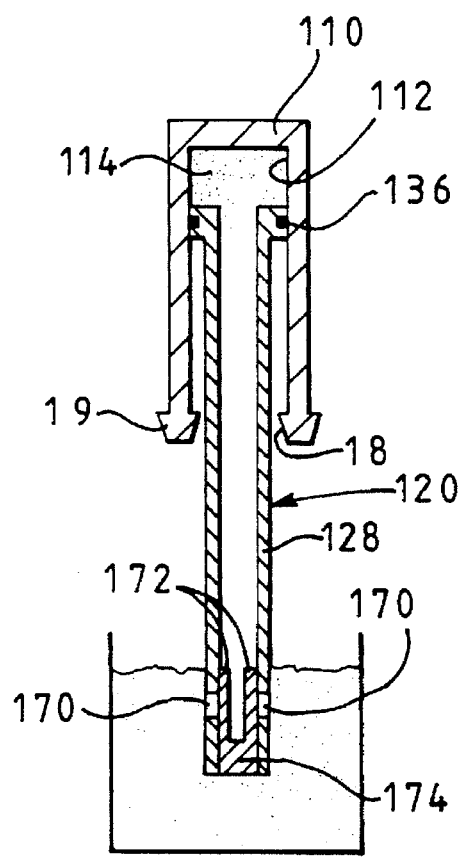

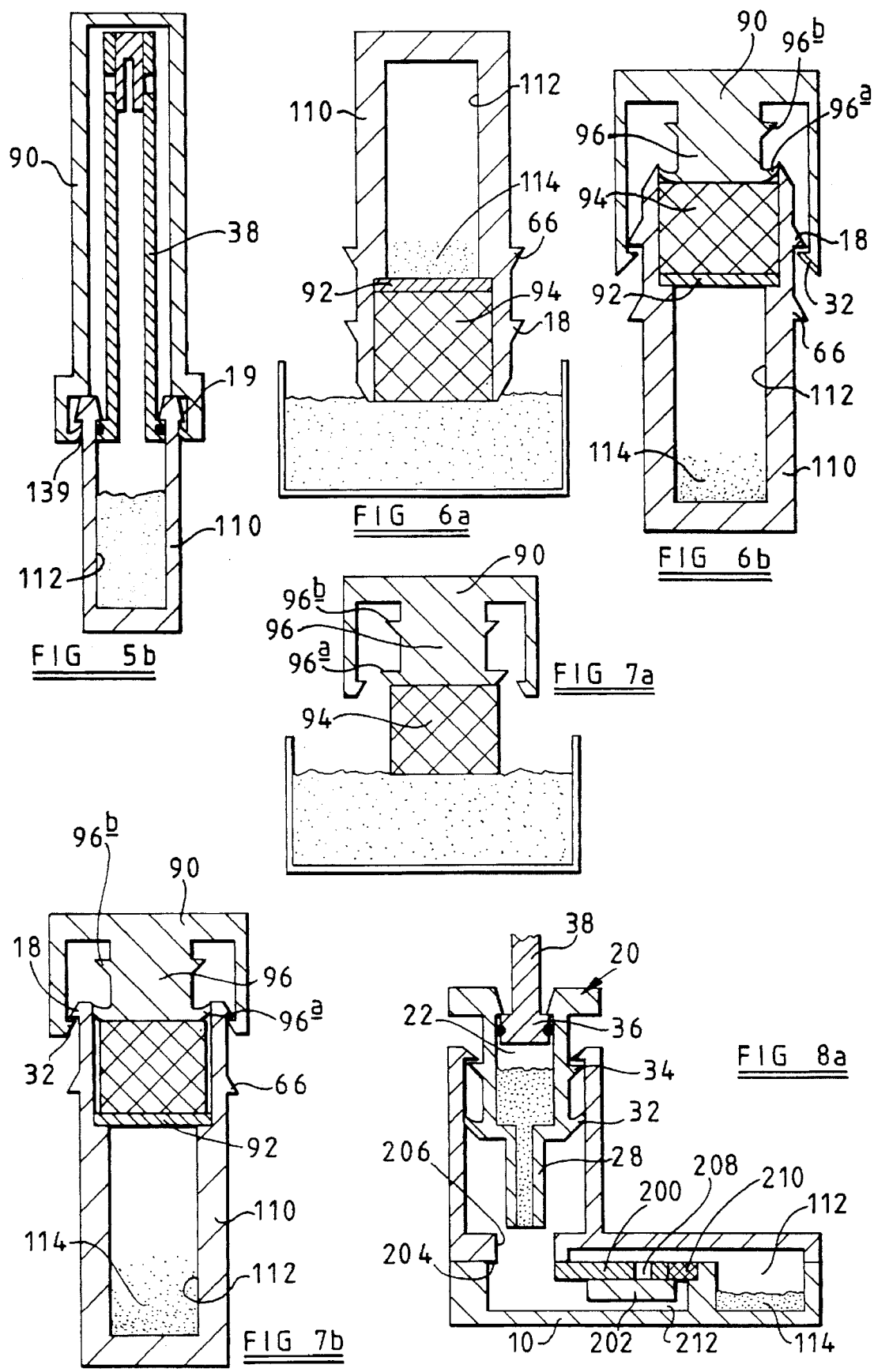

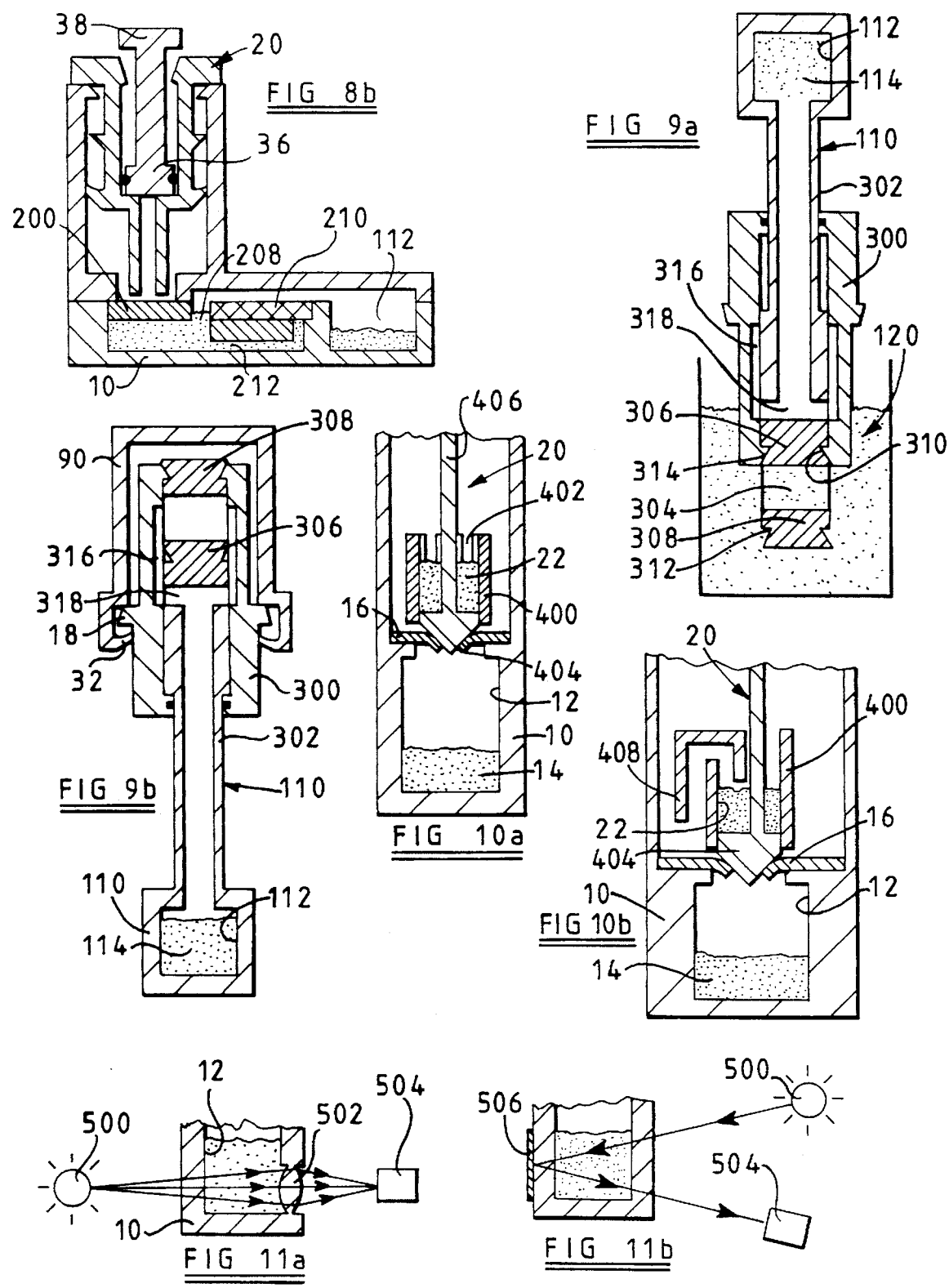

5,658,531

1

ASSAY DEVICE

This invention relates to an assay device and is more particularly concerned with a disposable assay device which is relatively safe and convenient to use and dispose of, and in which there is a reduced risk of operator contamination from either the assay reagents, or the sample to be analysed, or the resultant reaction mixture. This invention is particularly, but not exclusively, concerned with a disposable assay device for assaying for nicotine metabolites in samples of urine for the purpose of checking on recent smoking habit.

BACKGROUND OF THE INVENTION

The treatment of smoking-related disease is a major expenditure and there is a need for a convenient accurate determination of patient's smoking habit in order to determine appropriate and effective treatment of smoking-related diseases. There is also a demand for an assay device which can be used by non-chemists in extra-laboratory situations such as doctors surgeries, anti-natal clinics, industrial plants, water works, farms or the home. In order to be suitable for this, it is important for the assay device to be relatively easy and safe to use and to be relatively safely disposed of.

SUMMARY OF THE INVENTION

It is an object of the present invention to provide an assay device which meets the above-mentioned demand.

According to the present invention, there is provided a disposable assay device for assaying a sample, comprising a body including a reaction chamber which contains or is adapted to receive an assay reagent sensitive to a component being assayed for in the sample, a sample collector/dispenser for collecting a sample to be assayed and for dispensing a predetermined quantity of sample into the reaction chamber, said body and said collector/dispenser being non-detachably engaged or engageable together, and means for sealing the assembly of body and collector/dispenser to prevent leakage of the contents of the reaction chamber after use.

In a first series of embodiments, the sample collector/dispenser is adapted to be non-detachably engaged with said body after a sample has been collected, and the sealing means acts between the body and the collector/dispenser.

In this first series of embodiments, it is preferred for the sample collector/dispenser to include a sample collection cheer defined between two relatively moveable parts such that relative movement of the parts in one direction causes said predetermined quantity of the sample to be dispensed therefrom into the reaction chamber.

In one arrangement, the sample to be assayed is caused to enter a reservoir in which it is retained until being dispensed therefrom. In one aspect, the reservoir is defined by the cylinder of a piston and cylinder device so that the sample can be aspirated into the reservoir and then dispensed therefrom by relative movement of the piston and cylinder. In another aspect, the reservoir is filled by immersing it in the sample to be collected and causing the sample to be retained by closing the reservoir or designing the reservoir so that it retains the sample therein by surface tension. In the latter case, the surface tension effect can be achieved by providing the reservoir in a relatively narrow bore tube having a lower opening and having an upper opening which is openable to allow the sample to be collected and dispensed, but closed to retain the sample therein. In an alternative arrangement, the surface tension effect is achieved by filling the reservoir with a wicking element comprising an absorbent material which can be compressed to dispense sample absorbed therein.

The reaction chamber itself may be closed by a pierceable or moveable membrane.

The membrane may be a multi-layer construction and incorporate one or more reagents in order to enclose and separate it/them from other reagent(s). This multi-layer form of construction is useful for reagents which, when mixed together, can be unstable and must be kept separate prior to use.

In a second series of embodiments, the body and the collector/dispenser are permanently non-detachably engaged together and the collector/dispenser has an inlet which is opened to collect a sample, said inlet being closable by the means for sealing the assembly. In such an arrangement, the sealing means preferably comprises a cap which is engageable over that part of the collector/dispenser having the inlet so as to seal the assembly permanently.

The disposable assay device of the present invention is preferably supplied with the assay reagent therein, most preferably in solid form for use with a liquid sample. The assay reagent is preferably one which is designed to assay for nicotine metabolites. Most preferably, the assay reagents are arranged to assay for cotinine and equivalents thereof using a colorimetric assay based on the Koenig reaction (see for example Clinica Chimica Acta, 196 (1991) 159–166 or Thorax 1985;40;351–357).

BRIEF DESCRIPTION OF THE DRAWINGS

Embodiments of the present invention will now be described, by way of example, with reference to the accompanying drawings, in which:

FIG. 1a is an axial section through an assay device according to one embodiment of the present invention, FIG. 1b is an axial section showing a detailed modification of the device of FIG. 1a, FIG. 1c is an axial section through an alternative membrane arrangement to that illustrated in FIG. 1a, FIG. 2 is an axial section through a second embodiment of assay device according to the present invention, FIG. 3 is an axial section through a third embodiment assay device according to the present invention, FIG. 4a and FIG. 4b are axial sections through a fourth embodiment of an assay device according to the present invention, showing the device in different conditions, FIGS. 4c and 4d are scrap sections showing alternative detail modifications of the device of FIGS. 4a and 4b, FIG. 4e is an axial section through a further alternative, FIGS. 5a and 5b are axial sections through a fifth embodiment of assay device according to the present invention, showing the device in different conditions, FIG. 6a is an axial section of part of an assay device according to a sixth embodiment of the present invention, FIG. 6b is an axial section through the assembled assay device according to the sixth embodiment, FIGS. 7a and 7b are axial sections showing an assay device according to a seventh embodiment, FIGS. 8a and 8b are axial sections through an assay device according to an eighth embodiment of the present invention, showing the device in two conditions.

FIGS. 9a and 9b are axial sections through a ninth embodiment of an assay device according to the present invention, FIG. 10a is an axial section through part of a tenth embodiment of assay device according to the present invention, FIG. 10b is an axial section showing a modification of the device of FIG. 10a, and FIGS. 11a and 11b are views showing methods of using an assay device according to the present invention.

DESCRIPTION OF PREFERRED EMBODIMENTS

Referring now to FIG. 1a, the assay device illustrated therein comprises an open-topped elongated cylindrical body 10 having a reaction chamber 12 defined at its closed lower end. The reaction chamber 12 contains solid assay reagents 14 and is closed at its top by a pierceable membrane 16. The reagents may be loose within the chamber 12, immobilized onto the walls thereof, or applied to a separate member such as a disc of filter paper-like material disposed in the chamber 12. At its open upper end, the body 10 is provided with an integral, inwardly directed annular lip 18 having an upwardly presented lead-in ramp surface 18a and a radially directed rear (or lower) abutment surface 18b.

The assay device further comprises a sample collector/dispenser 20 having a sample collection chamber 22 closed by an elastic membrane 24. The collector/dispenser 20 has an upstanding wall 26 to facilitate grasping thereof without accidental depression of the membrane 24. The collector/dispenser 20 further includes a downwardly projecting sampling and piercing tube 28 which opens into the chamber 22 through lateral apertures 29 in a hollow volume-determining stop 30. The stop 30 is disposed within the chamber 22 and serves to limit downward depression of the elastic membrane 24. The collector/dispenser 20 has an outwardly directed annular seal 32 which cooperates with the internal surface of body 10 to provide a sliding seal arrangement between the body 10 and the collector/dispenser 20. The collector/dispenser 20 also has an outwardly directed rib 34 adjacent its lower end but above the seal 32. The rib 34 has a lead-in lower ramp surface 34a and an upper surface 34b (as viewed in FIG. 1a) which extends radially outwardly.

The assay device illustrated in FIG. 1a is supplied with the body 10 and sample collector/dispenser 20 completely separated. A sample to be assayed is aspirated into chamber 22 by dipping the tube 28 into the liquid after depressing membrane 24 until it abuts the stop 30, followed by release of the membrane 24 to draw the sample into the chamber 22. The collector/dispenser is then carried by means of the upstanding wall 26 taking care not to touch the membrane 24 and fitted into engagement with the body 10 so as to adopt the position illustrated in FIG. 1a. Hence, the seal 32 is forced past the inwardly directed lip 18 followed by the outwardly directed lip 34. The shape of the seal 32 and the provision of the ramp surfaces 18a and 34a assist in engagement of the collector/dispenser 20 with the body 10 but prevent subsequent detachment of these two parts, whilst the seal 32 ensures that a proper seal is provided between these two parts. The provision of the lips 18 and 34 also assists in providing a seal as well as providing abutment surfaces to prevent detachment of the parts without actually destroying either or both.

The collector/dispenser 20 is then urged downwardly from the position illustrated in FIG. 1a until the tube 28 has pierced the membrane 16. Finally, the elastic membrane 24 is depressed until it abuts against the stop 30, thus dispensing a predetermined quantity of the liquid sample into the reaction cheer 12. The contents of the reaction cheer 12 can then be mixed and the assay results visualised through the wall of the body 10 which is transparent at least in the region of the reaction chamber 12.

Instead of visualising the results, e.g. by direct observation of colour change in the reaction mixture, it is possible to introduce the assay device into a suitable colorimeter or the like to provide an automatic reading of colour change or change in turbidity. Once assaying has taken place, it will be appreciated that the device can be disposed of with a minimum risk of leakage of the contents of the device by reason of the sealing of the body 10 relative to the collector/dispenser 20. The non-detachable engagement of these parts ensures that access to the interior can only be gained actually by destroying one or other of the parts and that this can be made quite difficult.

As shown in FIG. 1b, the tube 28 may include a constriction 28a adjacent its lower end to prevent premature loss of liquid prior to dispensing.

As shown in FIG. 1c, the piercable membrane 16 is a multi-part membrane composed of upper and lower membranes 16a and 16b which are supported in spaced relationship by an annulus 16c. A chamber 17 is defined between the two membranes 16a and 16b for a further reagent 14a which is to be kept separate from the reagent(s) 14 illustrated and described above in relation to FIG. 1a. When the membrane 16b is ruptured by piercing tube 28 of collector/dispensor 20, the reagent 14a is mixed with the reagent(s) 14 and with the sample being assayed which is dispensed through the piercing tube 28.

As shown in FIG. 2, where similar parts to those of the embodiment of FIG. 1a are accorded the same reference numerals, instead of providing an elastic membrane 24, collector/dispenser 20 may resemble a convention syringe and therefore include a slidable piston 36 for aspirating liquid samples through tube 28 into chamber 22 and for dispensing the contents of the chamber 22 into the reaction chamber 12 after piercing the membrane 16. Manually depressible piston rod 38 is provided for this purpose and may include a localised weakened region 40 to enable the rod 38 to be snapped off after use to prevent the device from being opened. Alternatively, a latch 42 may be provided for latching the piston rod 38 in the closed position. Removal of the piston 36 is prevented by circular barbs 41 around the open end of the cylinder of the collector/dispenser 20.

In FIG. 3, tube 28 is mounted on the piston 36 and communicates with chamber 22 through an upper hole 44 at the underside of piston 36. The chamber 22 is defined by a cup-shaped body 46 whose upper surface is welded to the underside of a cap 48. A lateral hole 50 passes through the wall of the body 46 adjacent the underside of the cap 48. In this embodiment, lip 18 with upwardly directed ramp surface and downwardly directed radial abutment surface projects externally of the body 10 around the open end thereof. Cap 48 has inwardly directed seal 39 which forms a sliding seal with the external cylindrical surface of body 10 and which coacts with the lip 18 to prevent disengagement of the cap 48 from the body once the two parts have been engaged together.

A liquid sample to be assayed can be aspirated into the chamber 22 by dipping tube 28 into the sample with the body 46 and piston 36 mutually arranged so that piston 36 lies against the base of the body 46. In this condition, downward pressure on cap 48 causes movement of the body 46 relative to the piston 36 and aspiration of the sample through the tube 28 until the piston 35 clears the whole 50. Once this has happened, a reduced pressure no longer exists within the chamber 22 and so aspiration ceases. When tube 28 is removed from the liquid, it substantially drains. The collector/dispenser 20 is then carefully manoeuvred into position to engage the cap 48 with the body 10 so that initially the parts adopt the mutual positions illustrated in FIG. 3. Subsequently, the piston rod 38 is depressed in order to cause the tube 28 to pierce the membrane 16. This action brings the hole 44 to the bottom of the chamber 22, thus allowing the sample contained in the chamber 22 to dispense through the tube 28 into the reaction chamber 12 for mixing with assay reagents 14 therein.

Referring now to FIGS. 4a and 4b, the assay device illustrated therein has collector/dispenser 20 formed with cap 48 carrying rod 38 with sample collection chamber 22 in its lower end. A vent hole 60 fitted with a hingedly mounted flap valve 62 is provided at the top of the chamber 22. The cap 48 has a porous vent plug 64 therein formed of a suitable hydrophobic porous material, such as Zitex (Norton Performance Plastics, New Jersey, USA) which allows air to pass but not low pressure liquids.

In use, the lower end of rod 38 is dipped into the liquid sample to be assayed so that the chamber 22 is disposed below the surface of the sample. The liquid sample is permitted to enter the chamber 22 because air therein is vented through the vent hole 60, as permitted by the flap valve 62. However, when the collector/dispenser 20 is removed from the sample, the valve 62 closes and prevents escape of the sample from chamber 22. The collector/dispenser 20 is then engaged with the body 10 to adopt the position shown in FIG. 4a. In this condition, seal 39 within cap 48 has been forced past lip 18 and is sealingly slidable over the body 10. The cap 48 is then depressed so that the lower end of rod 38 is caused to puncture the membrane 16. Once the device has been moved into the condition illustrated in FIG. 4b, the flap valve 62 has abutted against the part of the membrane 16 surrounding the rod 38 and is thereby deformed so as to open the vent hole 60 which then allows the sample within chamber 22 to be dispensed under the action of gravity into the reaction chamber 12 and mixed with the assay reagents 14. In the position illustrated in FIG. 4b, the seal 39 has moved past a further lip 66 which is similar in construction to lip 18. Mutual engagement of the seal 39 and lip 66 retains the device in the condition illustrated in FIG. 4b in a non-detachable manner. Pressure which builds up within the cap 48 as a result of depression of the latter from the position illustrated in FIG. 4a to that illustrated in FIG. 4b is relieved by venting through the plug 64. In place of plug 64, a one-way valve may be provided (not shown). Either form of venting device may be used, if desired, in any of the other embodiments described herein.

In the place of flap valve 62, a non-return valve may be provided in simple form comprising merely a band of paper held around the outside of the conduit. Both the flap and the band may be of a fibrous material such as the type of paper commonly used for making paper towels.

In FIG. 4c, flap valve 62 is replaced by a plug 68 of porous material such as cotton wool so to act in a similar way to a paper band. Alternatively, the plug 68 may be formed of a compressed foam, such as polyvinyl alcohol, which expands when wetted and which projects from the side of the rod 38 so as to be removed automatically upon depression of the cap 48 into the position illustrated in FIG. 4b.

In FIG. 4d, the rod 38 containing chamber 22 terminates in a castellated end which allows easier piercing of the membrane 16 and which enhances the surface tension effect, thus further protecting the sample within chamber 22 from premature dispensing. As an alternative, a constriction may be provided at the bottom end of chamber 22 in a similar manner to the constriction 28a provided in tube 28 (FIG. 1b).

In FIG. 4e, the rod 38 is provided with grooves 69 at the lower end. These provide a means of sampling the material to be analysed. The grooves 69, in the case of a liquid sample, provide retention due to surface tension forces and substantially define the volume of sample therein. The rod 38 has a pointed lower end 70 to assist in piercing of the membrane. In this construction, the reagents would normally be in liquid form to allow the sample to dispense from the grooves. Furthermore, this embodiment may be used for sampling semi-solids such as faeces. In this case, the membrane coacts with the grooves to remove excess sample and hence the sample volume is defined principally by the volume of the grooves.

Referring now to FIGS. 5a and 5b, the assay device illustrated therein has collector/dispenser 120 permanently connected with body 110. Tube 128 is integrally joined with hollow piston 136 and permanently communicates with reaction chamber 112 in which solid assay regents 114 are provided. If desired, a perforated plate or plug may be provided in piston 136 to prevent the assay reagents 114 from falling into tube 128 but to allow permeation of the sample into the reaction chamber 112. The lower end (as viewed in FIG. 5a) of body 110 is provided with an inwardly directed annular lip 18 of similar construction to that described above in relation to FIG. 1a, and an outwardly directed annular rib 19 to similar construction. The rib 18 permits the piston 136 to be forced into the body 110 during initial assembly of the assay device and to retain it thereafter.

The lower end of tube 128 is provided with opposed liquid inlet holes 170 which are closed by respective lobes 172 of a non-return valve body 174 inserted into the lower end of tube 128. In use, a liquid sample to be assayed is aspirated by immersing the apertures 170 in the liquid and then withdrawing the body 110 upwardly relative to tube 128. If desired, markings may be provided on the outside of the tube 128 to indicate the level to which the sample has to be aspirated in order to enable the required quantity of sample to be taken. Alternatively, the piston 136 may cooperate with internal stops (not shown) in the body 110 to provide a pre-set amount of aspiration. The lobes 172 prevent loss of sample from the tube 128. Thereafter, the whole assembly is inverted to adopt the position illustrated in FIG. 5b, and a cap 90 is snap-fitted into position so as to seal the whole assembly in a non-detachable way. The cap 90 completely overlies the rod 128 and has a seal 139 which coacts with rib 19 in a similar way to that in which the seal 39 coacts with lip 18 in the embodiment of FIG. 3.

In the embodiment of FIGS. 6a and 6b, body 110 has chamber 112 containing solid assay reagent 114 closed by a liquid-permeable support plate 92 which separates the reaction chamber 112 from a compressible absorbent pad 94 provided within the body 110 at the open end thereof. The assay device of FIGS. 6a and 6b further comprises cap 90 with inwardly directed lip 32 and plunger 96 with seals 96a and 96b.

In use, body 110 is inverted so as to contact the exposed portion of the absorbent pad 94 with the sample to be assayed which is drawn into the absorbent pad until the latter is saturated therewith. The body 110 is then withdrawn and inverted to the position illustrated in FIG. 6b. Cap 90 is then snap-fitted onto body 110 and pressed firmly down so as to compress the absorbent pad 94 and thereby force a predetermined quantity of the sample to be assayed through the liquid-permeable plate 92 and into the reaction chamber 112 to be mixed with the assay reagent 114 therein. The seals 96a and 96b ensure that the assembly is fully sealed and the engagement of the lip 32 first with the lip 18 and finally with the lip 66 ensures that the cap 90 is non-detachably engaged with the body 110 for safe disposal of the assay device after use.

FIGS. 7a and 7b show a similar embodiment to that described above in relation to FIGS. 6a and 6b. In this embodiment, however, the absorbent pad 94 is secured to the end of plunger 96 on cap 90 and is compressed against liquid-permeable plate 92 in body 110 to dispense a predetermined quantity of the liquid sample to be assayed into reaction chamber 110.

In FIGS. 8a and 8b, a collector/dispenser 20 similar to that illustrated in FIG. 2 is utilised. In this embodiment, however, body 10 is of generally L-shaped form and is provided with a slide valve arrangement comprising a slidable valve plate 200 carried on support 202 and cooperating with an annular seat 204 around a sample entrance hole 206 aligned with tube 28. The plate 200 is provided with a passage 208 therethrough which, in the condition illustrated in FIG. 8a, is closed by support 202. The plate 200 is moveable by means of a compressed foam pad 210 formed, for example, of polyvinylalcohol foam which expands when wetted. It is to be appreciated that, in the position illustrated in FIG. 8a, the valve plate 200 completely closes the chamber 112 from the remainder of the body 10 and that the pad 210 is shown in its compressed (i.e. unwetted condition). The assay reagents 114 are in dry solid form.

When a predetermined quantity of liquid sample to be assayed has been dispensed from the collector/dispenser 20 by depression of piston rod 38, the sample passes through hole 206 and travels along a shallow passage 212 to wet the compressed pad 210. This expands the pad 210 and moves the plate 200 to the left as viewed in FIG. 8a until it adopts the position illustrated in FIG. 8b where the entrance hole 206 is sealed by the plate 200 and where the sample to be assayed can enter the reaction chamber 112 through hole 208 when the device is tipped. It will be appreciated that, at no stage before, during or after use of the device, is external access to the reagents 114 permitted. As with previously described embodiments, the collector/dispensor cannot be removed.

In FIGS. 9a and 9b, an arrangement which is somewhat similar to that described above in relation to FIGS. 5a and 5b is illustrated. In this embodiment, instead of a predetermined quantity of sample to be assayed being aspirated into collector 20, a predetermined quantity of sample is taken without application of reduced pressure. In this device, a sleeve 300 has a hollow plunger 302 slidable therein. The distal end of plunger 302 (i.e. that end remote from chamber 112) has a transverse bore 304 therethrough. Above and below the bore 304 (as viewed in FIG. 9a), the plunger 302 has lands 306 and 308, respectively, with grooves 310 and 312 therein. The grooves 310 and 312 have their lower surfaces chamfered and their upper surfaces extending substantially radially of the respective lands 306 and 308. As shown in FIG. 9a, groove 310 cooperates with a correspondingly shaped lip 314 provided internally of sleeve 300. In this condition, transverse bore 304 is disposed externally of sleeve 300 so that it can be completely filled with sample to be assayed when the distal end of the device is immersed in the sample. When this has taken place, the plunger 302 is manually lifted so as to bring the groove 312 into engagement with the lip 314. Such movement is permitted because of the relative shapes of the grooves 310 and 312 and the lip 314, but movement in the opposite direction is not permitted. It will thus be appreciated that a predetermined quantity of the sample to be assayed is thereby collected, such quantity corresponding to the volume of the transverse bore 304. When the device is inverted to the position shown in FIG. 9b, the sample in the bore 304 is free to enter the reaction chamber 112 by passing through a channel 316 defined within sleeve 300 and into a further transverse bore 318 defined at the opposite side of land 306 no transverse bore 304.

The distal ends of the plunger 302 and sleeve 300 are sealed closed by cap 90 in an non-detachable way by virtue of the provision of inwardly directed sealing lip 32 at the open end of cap 90 which seals with the outer peripheral surface of sleeve 300 on which outwardly directed chamfered lip 18 is provided.

In FIG. 10a, collector/dispenser 20 comprises slidable sleeve 400 with castellations 402 at its upper end provided for a similar purpose to that described above in relation to FIG. 4d. Within sleeve 400 is defined chamber 22. The sleeve 400 is detachably supported by a downwardly directed conical member 404 carried on actuating rod 406. A predetermined quantity sample to be assayed is taken by immersing the sleeve 400 and conical member 404 in the sample and then transferring it to the body 10. Downward pressure on the plunger 406 causes the conical member 404 to pierce the membrane 16 and engagement of the sleeve 400 with the pierced membrane 16 and its support causes separation of the conical member 404 from the sleeve 400 and thereby dispensing of the sample within chamber 22 into the reaction chamber 12 for mixing with the assay reagents 14.

The upper end of the body 10 (i.e. that end which is not illustrated) is non-detachably closed and sealed by a cap which may be similar to those described herein above in relation to, for example, FIGS. 3 or 4a and 4b.

In FIG. 10b, an arrangement similar to that illustrated in FIG. 10a is provided and similar parts are accorded the same reference numerals. However, in FIG. 10b, spillage is minimised and sample volume determined by the provision of a siphon arrangement 408 through which chamber 22 is initially filled with the sample.

In FIGS. 11a and 11b are shown two ways of enabling colorimetric assays. In FIG. 11a, body 10 in the region of reaction chamber 12 is completely transparent and so can be traversed by light rays emanating from a convenient light source 500. The lights rays may be condensed by lens 502 to enter detector 504 for producing an output which gives an indication of the absorbance resulting from passage of the light rays through the reaction mixture in reaction cheer 12.

In FIG. 11b, a similar arrangement is shown except that the light rays are reflected from a mirror 506 so that each light ray passes twice through the reaction mixture so that the effective optical path length through the latter is doubled. It is within the scope of the present invention, however, to observe the change in optical properties of the reactants by eye rather than automatically by a machine.

In the case where the above-described assay reagents are used for assaying nicotine metabolites in urine, the sample to be assayed is urine and the assay reagents comprise:

| | |
|---|---|
| 1. Citric acid (2M/Sodium citrate (1.5M)/buffer pH 4.7) | 150 µl, |
| 2. Potassium cyanide (20%) | 50 µl, |

-continued

| | |
|---|---|
| 3. Chloramine - T (20%) | 50 μl, |
| 4. Thiobarbituric acid (10%) | 500 μl, | to which is added 500 μl of urine (Modification of Peach et al—Thorax 1985;40:351–7).

We claim:

1. A disposable assay device for assaying a sample comprising:
   a body having a reaction chamber for receiving an assay reagent sensitive to a component being assayed for in the sample, said reaction chamber being closed by a pierceable membrane;
   a sample collector/dispenser having means for collecting the sample to be assayed and a means for dispensing a predetermined quantity of the sample collected into the reaction chamber of the body, said dispensing means having a downwardly projecting sampling and piercing tube;
   means for non-detachably engaging said body with said collector/dispenser; and
   a means for sealing said body with said collector/dispenser when non-detachably engaged to prevent leakage of a collected sample, reagent and mixtures thereof from said reaction chamber.

2. The device of claim 1 wherein said collector/dispenser is non-detachably engaged with said body after said sample has been collected and the sealing means acts between said body and said collector/dispenser.

3. The device of claim 1 wherein said means for collecting said sample comprises a reservoir for receiving the sample to be assayed and for retaining said sample until being dispensed therefrom.

4. The device of claim 3 wherein said reservoir is defined by a hollow piston and a cylinder device such that the sample is aspirated into the reservoir and subsequently dispensed therefrom by relative movement of the piston and cylinder.

5. The device of claim 4 wherein the cylinder is arranged to be filled by immersing said reservoir in the sample to by collected and to retain the sample therein.

6. The device of claim 3 wherein the cylinder is arranged to be filled by immersing said reservoir in the sample to be collected and to retain the sample therein by surface tension.

7. The device of claim 1 wherein said membrane has a multi-layer construction.

8. The device of claim 1 wherein, when said body and said collector/dispenser are non-detachably engaged, said collector/dispenser has an inlet which is open for collecting said sample and is closeable by said means for sealing said body with said collector/dispenser.

9. The device of claim 8 wherein said means for sealing said body with said collector/dispenser comprises a cap which is engageable over said inlet of said collector/dispenser for permanently sealing said body with said collector/dispenser.

10. The device of claim 1 further comprising an assay reagent.

11. The device of claim 10 wherein said assay reagent is for assaying nicotine metabolites.

12. A disposable assay device for assaying a sample, said assay device comprising:
   (1) a hollow body defining a reaction chamber for receiving an assay reagent sensitive to a component being assayed for in the sample, said hollow body having an opening therein;
   (2) a sample collector/dispenser which is separate from said hollow body but engageable therewith, said collector/dispenser being for collecting a sample to be assayed and for dispensing a predetermined quantity of the sample collected, said sample collector/dispenser comprising:
      (a) a sample collecting chamber having a tube with an opening therein for collecting the sample when the collector/dispenser is separated from said hollow body, said tube being of a size to be inserted into said hollow body through said opening in said hollow body so that the predetermined quantity of the sample collected can be dispensed from said sample collecting chamber into said reaction chamber when said collector/dispenser is engaged with said hollow body, and
      (b) aspirating/dispensing means for aspirating the sample through said tube into said sample collecting chamber and dispensing the sample collected through said tube; said sample collecting chamber and said aspirating/dispensing means being non-detachably secured together;
   (3) mutually interengageable lip and ramp formations on said sample collector/dispenser and said hollow body to enable said sample collector/dispenser and said hollow body to be non-detachably secured together with said tube of said sample collector/dispenser inserted into said hollow body; and
   (4) a seal arrangement which seals said hollow body to said collector/dispenser when said sample collector/dispenser and said hollow body are non-detachably secured together so as to prevent leakage of a collected sample, reagent and mixtures thereof from said reaction chamber.

13. The device of claim 12 wherein said reaction chamber is closed by a slidable plate.

14. The device of claim 12 wherein said reaction chamber is closed by a puncturable membrane.

* * * * *